United States Patent
Siljamaki et al.

(10) Patent No.: US 7,609,811 B1
(45) Date of Patent: Oct. 27, 2009

(54) METHOD FOR MINIMIZING THE TONGUE AND GROOVE EFFECT IN INTENSITY MODULATED RADIATION DELIVERY

(75) Inventors: Sami Pekka Siljamaki, Helsinki (FI); Katja Marika Pesola, Vantaa (FI)

(73) Assignee: Varian Medical Systems International AG, Zug (CH)

( * ) Notice: Subject to any disclaimer, the term of this patent is extended or adjusted under 35 U.S.C. 154(b) by 0 days.

(21) Appl. No.: 12/267,044

(22) Filed: Nov. 7, 2008

(51) Int. Cl.
*A61N 5/10* (2006.01)
*G21K 1/02* (2006.01)
(52) U.S. Cl. .................................. 378/65; 378/147
(58) Field of Classification Search ......... 378/145–153, 378/62, 65
See application file for complete search history.

(56) References Cited

U.S. PATENT DOCUMENTS

| | | | |
|---|---|---|---|
| 5,847,403 A * | 12/1998 | Hughes et al. | 250/505.1 |
| 6,661,871 B2 * | 12/2003 | Siochi | 378/65 |
| 7,257,196 B2 * | 8/2007 | Brown et al. | 378/150 |
| 2005/0254623 A1 * | 11/2005 | Kamath et al. | 378/65 |
| 2007/0127624 A1 * | 6/2007 | Seeber et al. | 378/147 |

* cited by examiner

*Primary Examiner*—Irakli Kiknadze
(74) *Attorney, Agent, or Firm*—Townsend and Townsend and Crew LLP

(57) ABSTRACT

The present invention provides an intensity modulated radiation therapy (IMRT) method for treating a target region that minimizes the tongue and groove effect. By minimizing that effect, striping in the final delivered fluence is reduced, which improves the overall quality of the radiation delivery. In the method, compensating functions $C_i(x)$ are added to leaf coordinates $a_i(x)$ and $b_i(x)$ for all of the leaf pairs i in a leaf sequence algorithm, where $C_i(x)$ is chosen to match the mechanical limitations of the MLC and to minimize non-weighted or weighted sums of the tongue and groove effects, where the weighting is time-dependent, position-dependent, or time- and position-dependent, or to minimize the total treatment time, changes to the original MLC sequence, or the tongue and groove effect distribution variance in spatial or temporal coordinates.

12 Claims, 6 Drawing Sheets

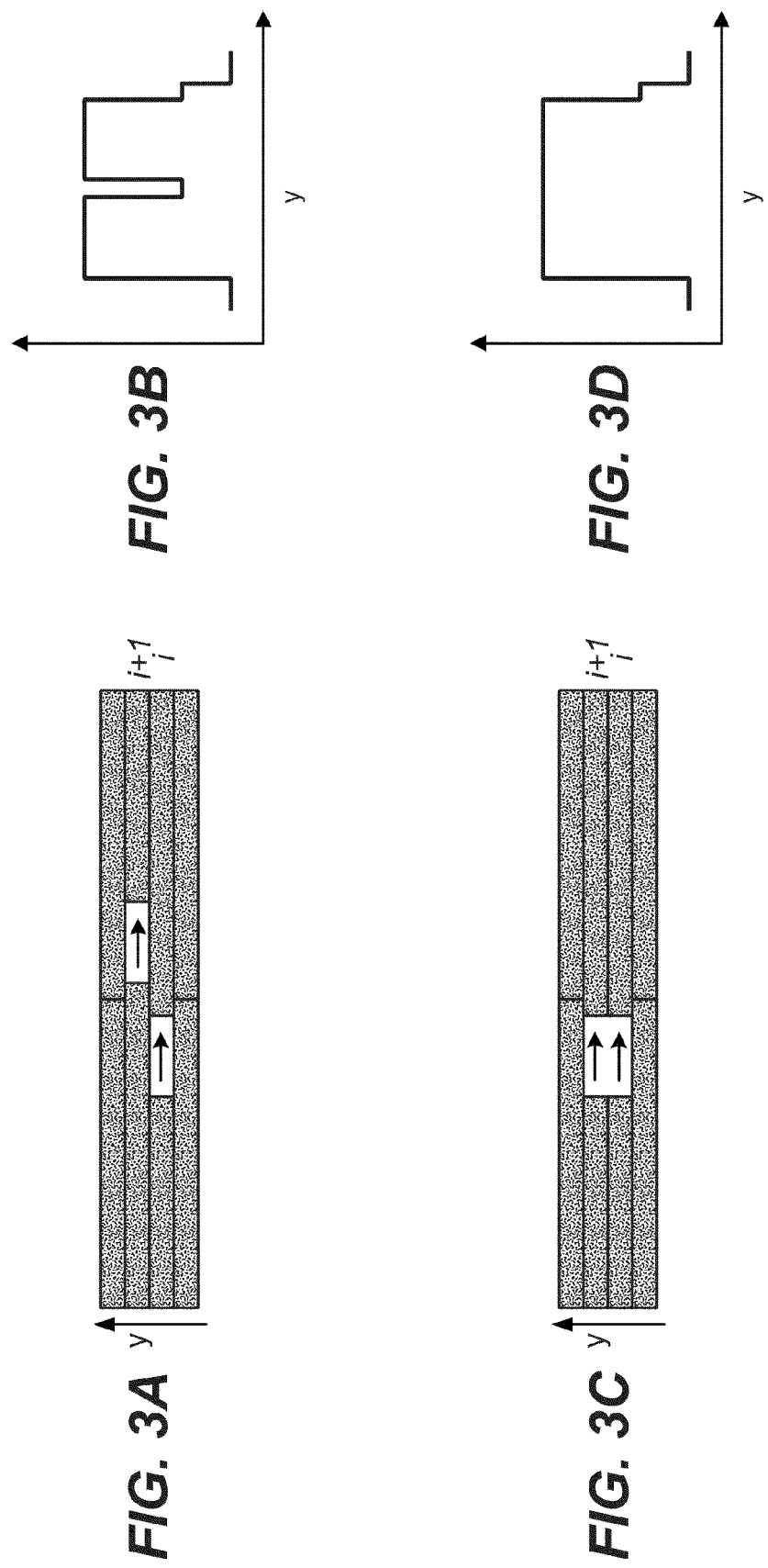

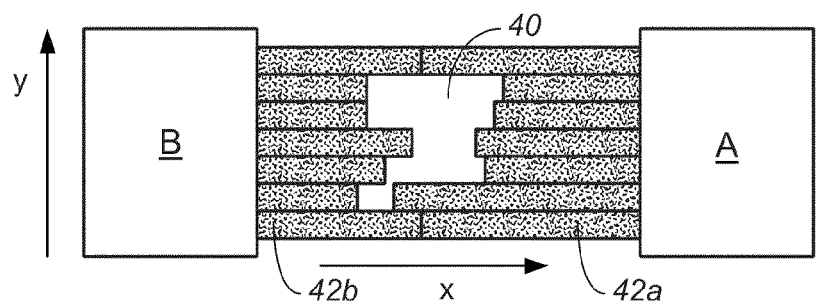
FIG. 4
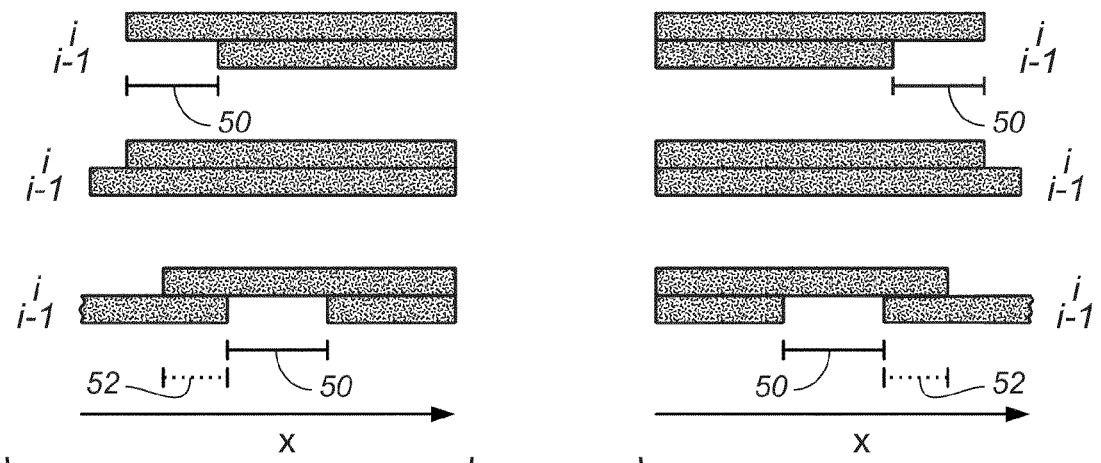
FIG. 5A  FIG. 5B
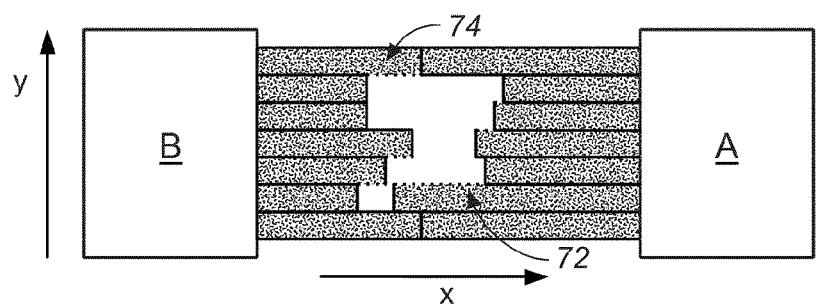
FIG. 7

METHOD FOR MINIMIZING THE TONGUE AND GROOVE EFFECT IN INTENSITY MODULATED RADIATION DELIVERY

FIELD OF THE INVENTION

The present invention is related to radiation therapy systems using multi-leaf collimators and is particularly related to a method for minimizing the tongue and groove effect that produces undesirable striping in the final delivered fluence for intensity modulated radiotherapy systems.

BACKGROUND OF THE INVENTION

Radiation therapy for cancer treatment has been in use for several decades. Modern radiation therapy systems typically generate high intensity x-rays by bombarding a suitable target with high energy electrons. X-rays are emitted from the target in a generally conical pattern and are initially confined to a generally rectangular beam by moveable, x-ray blocking "jaws" in the head of the system. Typically, the patient is positioned about 1 meter from the x-ray target and, when fully open, the jaws define a square treatment area that is about 40 cm×40 cm at the patient plane. Rarely, however, can the system jaws alone be used implement a suitable treatment plan. While high energy x-rays are used most commonly in radiotherapy, other types of radiation, including electron and proton beams are also known in the art. The nature of the radiation beam can have significant impact on the appropriate shielding and field shaping collimator designs, particularly for those particle beams that are not subject to an exponential attenuation but rather are stopped by successive interactions that cause energy loss. Application of the present invention, however, is not dependent upon use of any particular type of radiation beam, thus any type-specific descriptions are for exemplary purposes only.

It is usually desirable to irradiate only a precisely defined area or volume conforming to a tumor, and to irradiate the target site from multiple angles. Multi-leaf collimators (MLCs), such as described in the co-assigned U.S. Pat. No. 4,868,843, issued to Nunan (the disclosure of which is incorporated by reference), have been almost universally adopted to facilitate shaping of the radiation beam so that the beam conforms more closely to the site being treated, i.e., the beam is shaped to conform to the shape of the tumor from the angle of irradiation. Subsequent to its introduction, the MLC has also been used to perform a technique known as "Intensity Modulated Radiotherapy" (IMRT), which allows control over the radiation doses delivered to specific portions of the site being treated. In particular, IMRT allows the intensity distribution of the radiation reaching the patient to have almost any arbitrary distribution. MLCs are also used, for example, in arc therapy; wherein the gantry system, and hence the radiation beam, is moved along an arc while the patient is being irradiated.

The basic operation of an MLC is well known in the art and will not be described in detail. In summary, the MLC comprises moveable leaves that are positioned to create an opening or aperture that can be viewed as lying in a plane that is perpendicular to the general direction of radiation. The MLC aperture can have any arbitrary shape within the mechanical limits of the device, through which the radiation is delivered. Static IMRT (s-IMRT) can be implemented by iteratively positioning the leaves of an MLC to provide the desired field shapes. Superposition of the individual apertures, which typically number from one to hundreds, collectively delivers the desired dose distribution. This approach is static in the sense that the leaves do not move when the beam is on.

Alternatively, in systems such as those sold by the assignee of the present invention, a dynamic IMRT (d-IMRT) method can be implemented using, for example, a "sliding window" approach, in which the leaves of an MLC are moved continuously across the beam when the beam is on. Each leaf pair (44a, 44b in FIG. 4) creates a time-dependent opening that traverses the target area from one side to the other, creating the desired fluence pattern. By adjusting the speed of leaf motion and the separation of the leaves, different portions of the treatment field can be irradiated with different doses of radiation as prescribed in a treatment plan.

Although the leaves are positioned closely together, many MLCs have a problem with inter-leaf leakage, where radiation leaks through the space between the leaves. This leakage causes striping in the final delivered fluence, which is undesirable because it causes a variance between the delivered dose and the dose prescribed under the treatment plan. To minimize this inter-leaf leakage, some MLC models use leaves 10a with a tongue 12a and groove 14a design (see FIG. 1A). The tongue of each leaf fits into the groove of the adjacent leaf, blocking radiation from leaking between the leaves and, thereby, reducing striping in the final fluence delivery. Unfortunately, the tongue and groove design can also have the opposite effect; increasing the stripe patterns in the final fluence. This increase occurs when a tongue of one leaf is exposed, i.e., not positioned within the groove of another leaf, during delivery of radiation. The exposed tongue partially blocks radiation from passing, which causes a stripe in the final fluence.

Throughout this disclosure, the "tongue and groove effect" specifically refers to the negative effect in IMRT delivery that is caused by a thickness of leaf material on the side of a leaf exposed to the incident rays of the radiation beam that is less than the full thickness of the leaf. This thickness can be in the form of an exposed tongue, such as 12a in FIG. 1A, or an exposed groove, such as 14a, but is not limited to this type of leaf design. An "exposed" groove can be thought of as missing material to make room for an adjacent tongue with the remaining leaf material exposed to rays of the beam alone. Exposure of either a tongue or a groove can cause striping in the IMRT delivery. Depending on the geometry of the MLC, the striping caused by an exposed groove may be less significant than that caused by an exposed tongue (such as the leaf design in FIG. 1A), although in most current designs the effect from an exposed tongue is very similar to, if not the same as, the effect from an exposed groove.

The tongue and groove pattern can be at any height along the leaf side and need not be in the form of a centrally located groove 14a as shown in FIG. 1A. Some MLC designs employ a single stepped side wherein the tongue is a protrusion in one half of the leaf while the "groove" is a mating inset. Other MLC designs use a more symmetrical, slanted leaf pattern (e.g., 10b in FIG. 1B), where the effects of an exposed tongue 12b and a corresponding exposed groove 14b are of equal magnitude. In such a design, the exposed tongue and groove may simply be surfaces that protrude or recede with respect to the diverging beam rays by virtue of a purposeful difference between the divergence of the beam rays and the side of the leaf. Other leaf designs may be employed to reduce the effect of inter-leaf leakage that introduces a tongue and groove effect in IMRT. The present invention described below is applicable to any of these designs because although a tongue or groove feature may not be evident in the leaf design, the tongue and groove effect may nonetheless be observed in a resulting IMRT field.

While the tongue and groove effect may be used advantageously in certain advanced optimization techniques, such as in s-IMRT pattern calculation or d-IMRT minimum-leaf-gap-effect optimization (which may also be used in combination with the present method by limiting the area to which the method is applied), the tongue and groove effect generally has a negative impact on the quality of the delivery. In particular, current IMRT techniques at most evaluate the effect, but do not take it into account in leaf position calculations.

BRIEF SUMMARY OF THE INVENTION

The present invention provides an intensity modulated radiation therapy (IMRT) method for treating a target region that minimizes the tongue and groove effect. By minimizing that effect, striping in the final delivered fluence is reduced, which improves the overall quality of the radiation delivery.

The method of the present invention begins with an MLC sequence obtained from an external leaf-sequencing algorithm. After determining the mechanical limitations of the MLC, compensating functions $C_i$ are added to leaf coordinates $a_i$ and $b_i$ for all of the leaf pairs i. The compensating functions are selected such that mechanical limitations of the MLC are not exceeded and at least one of the following is minimized: a non-weighted sum of the tongue and groove effects, a weighted sum of the tongue and groove effects using time-dependent weighting, a weighted sum of the tongue and groove effects using position-dependent weighting, a weighted sum of the tongue and groove effects using time- and position-dependent weighting, the total treatment time, changes to the original MLC sequence, the tongue and groove effect distribution variance in spatial coordinates, or the tongue and groove effect distribution variance in temporal coordinates.

BRIEF DESCRIPTION OF THE DRAWINGS

FIG. 3A illustrates a leaf pattern producing striping in the final fluence delivery.

FIG. 3B is a representation of the fluence delivery from the leaf pattern in FIG. 3A.

FIG. 3C illustrates a leaf pattern that does not produce striping in the final fluence delivery.

FIG. 3D is a representation of the fluence delivery from the leaf pattern in FIG. 3C.

FIG. 4 shows a typical MLC arrangement of opposing leaf pairs.

FIGS. 5A and 5B show leaves from the right and left banks, respectively, of an MLC with the amount of exposed tongue indicated.

FIG. 7 shows a non-coplanar MLC having inverted tongues on each bank.

DETAILED DESCRIPTION OF THE INVENTION

Figure 1A:
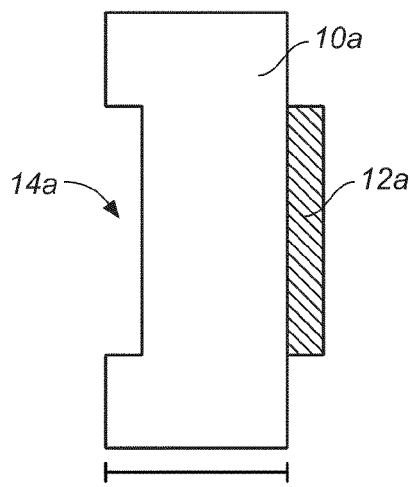
FIGS. 1A and 1B show two tongue and groove designs for MLC leaves: a stepped design (1A) and a non-stepped design (1B).
Figure 1B:
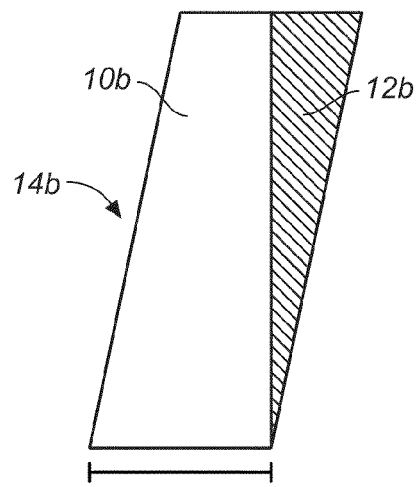

Certain conventions, described below, have been used throughout this disclosure and are helpful to the description of the present method.

The fluence through a multi-leaf collimator (MLC) is delivered at a dose rate D(t), where t is the real time and the dose rate may be variable with time. The time integral of D(t) is the function MU(t), which defines the relationship between the real time t and the number of monitor units delivered. However, to simplify notation in the description below, the dose rate is taken to be constant and the monitor units are denoted simply by t throughout.

FIG. 4 depicts a typical MLC arrangement. The individual leaves are grouped into a left bank B and a right bank A, with each leaf 42b forming a leaf pair with the corresponding leaf 42a on the opposing bank. Each leaf in a pair is individually moveable by a motor drive not shown. Individual leaf pairs are designated by indices i, which vary based on the pair's position. Continuing with FIG. 4, let $x=a_i(t)$ denote the position of the ith leaf tip on leaf bank A, and $x=b_i(t)$ denote the corresponding leaf tip on leaf bank B at time t. The orientation is chosen such that $a_i(t) \geq b_i(t)$. The aperture figures are drawn such that the x coordinate increases from left to right and they coordinate and the lead index i increase from bottom to top. For consistency, the tongues of each leaf pair are directed towards the lower indicied leaf pairs, although in practice the tongues could be oriented in either direction. Accordingly, in FIG. 4, the left bank B is located at a lower x coordinate and the right bank A at a higher x coordinate. Because the leaf indices increase from the bottom up, the tongues of leaves i+1 are directed toward leaves i.

The tongue and groove effect for a given MLC sequence may be calculated in two ways. First, the effect may be calculated as a function of time. The tongue and groove effect depends directly on the amount of tongue that is exposed during the sequence, thus it is necessary to calculate the total exposure. FIG. 5A shows sets of leaves from bank A (referred to as the "A leaves") in three configurations, having varying amounts of tongue exposed. The amount of tongue of leaf i visible in the aperture is shown by the solid bars 50 and corresponds to the difference between the leaves i and i−1, which is given by the expression $\max\{0, a_{i-1} - a_i\}$. It is also necessary to consider whether any of the otherwise exposed tongue has been covered by a leaf from the opposing bank, such as in the lowermost set of leaves in FIG. 5A. The expression $\max\{0, b_{i-1} - a_i\}$ represents the amount of tongue hidden by the opposite leaf, as is shown by the dotted bar 52. These expressions can be combined to reflect the amount of tongue from leaf i of bank A that is exposed at time t, which is given by $tng_i^a(t) = \max\{0, a_{i-1}(t) - a_i(t)\} - \max\{0, b_{i-1}(t) - a_i(t)\}$. The corresponding expressions for leaf i of bank B are $\max\{0, b_i - b_{i-1}\}$ and $\max\{0, b_i - a_{i-1}\}$ (FIG. 5B), which combine to produce the overall exposure equation of $tng_i^b(t) = \max\{0, b_i(t) - b_{i-1}(t)\} - \max\{0, b_i(t) - a_{i-1}(t)\}$.

Having the exposures for the individual leaves, the total exposure can then be calculated. Let $tng_i(t) = tng_i^a(t) + tng_i^b(t)$ and $$tng(t) = \sum_{i=2}^{N} tng_i(t).$$

The function tng(t) thus gives the total amount of tongue exposed in an aperture at time t. As the measure of the total tongue and groove effect of the whole treatment, the expression $TNG_i = \int tng_i(t)dt$ can be used for a leaf pair i, and $$TNG = \int tng(t)dt = \sum_i TNG_i$$

for the whole MLC sequence.

Second, the exposure may be calculated as a function of position x. The position refers to a coordinate along the leaf motion direction, and the perpendicular y coordinate has a value that corresponds to a "tongue area" or stripe in the fluence. Using the same expressions and indexing as above, the amount of tongue and groove effect caused by the A leaves and the B leaves at position x is $tng_i^a(x) = \max\{0, a_i(x) - a_{i-1}(x)\} - \max\{0, a_i(x) - b_{i-1}(x)\}$ and
$tng_i^b(x) = \max\{0, b_{i-1}(x) - b_i(x)\} - \max\{0, a_{i-1}(x) - b_i(x)\}$,
respectively. The total amount of tongue and groove for a given x value is $tng_i(x) = tng_i^a(x) + tng_i^b(x)$ and the total tongue and groove effect along the stripe corresponding to index i is $TNG_i = \int tng_i(x)dx$. This is equivalent to the expression derived above using time-dependent functions.

A compensating function C(x) that is added to a(x) or b(x) can, for example, be understood as a "delay function": it determines the amount of time that the leaf is delayed from the original time at position x. For a constant C, the effect is merely a shift on the time axis. A non-constant C(x) causes changes in the leaf speed. Such a delay function does not directly control the width of the opening because it operates on the x axis, while the openings are defined on the t axis.

Figure 2A:
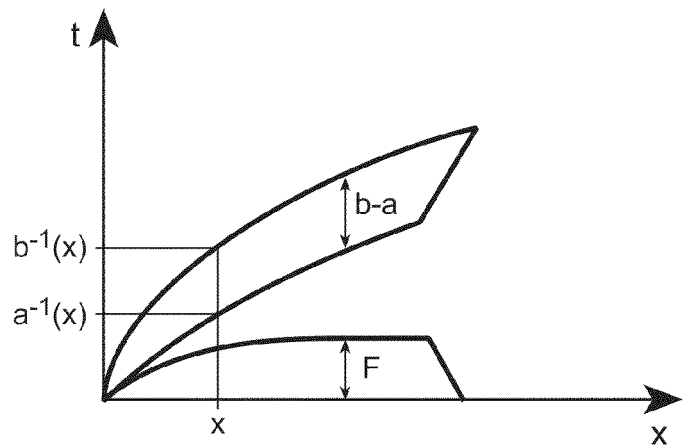
FIGS. 2A and 2B show a sample sliding window fluence delivery for a single leaf pair as a function of time (t) and position (x).
Figure 2B:
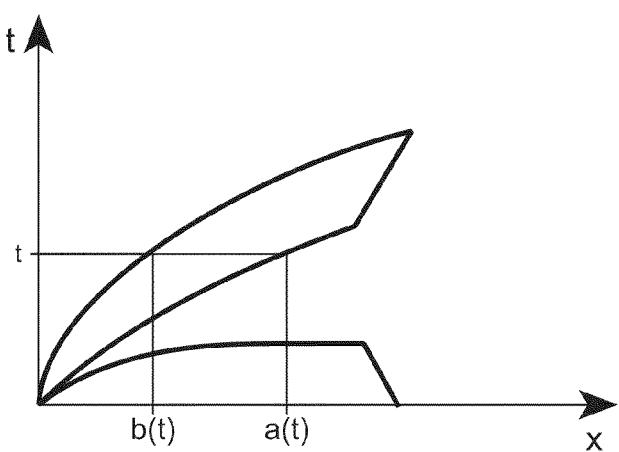

Minimization of the tongue and groove effect can be demonstrated using an example of a sliding window technique. To simplify the notation, the example assumes that the leaves have a 0% transmission rate, even at their tips, which is generally referred to as a 0/1 fluence. A sample sliding window delivery of the fluence for a single leaf pair is depicted in FIG. 2, where the sliding window is moving from left to right. The right and left trajectories, a(t) and b(t), respectively, are a function of the monitor units, which are the units of radiation output by the system, and the width of the opening between the leaves is given by a(t)−b(t) (FIG. 2B). The trajectories a(t) and b(t) are only fixed by the condition $b^{-1}(x) - a^{-1}(x) = F(x)$. Here, $a^{-1}(x)$ and $b^{-1}(x)$ are the trajectories as a function of the position x, which, in sliding window techniques, is well-defined. F(x) is the fluence to be delivered to position x. In other words, as shown in FIG. 2A, for a constant dose rate, the difference b−a is equal to the fluence F at position x. Thus, any arbitrary compensating function C(x) can be added to both $a^{-1}(x)$ and $b^{-1}(x)$ without changing the resulting output fluence. According to an embodiment of the present invention, a suitable C(x) for all leaf pairs is chosen such that the tongue and groove effect is minimized.

To demonstrate how the magnitude of the tongue and groove effect can be changed by selecting an appropriate C(x), FIG. 3 provides an example using two adjacent leaf pairs that are assumed to have a constant fluence (the same constant for both leaf pairs). In FIG. 3A, the constant fluence is produced when the opening i travels at a constant speed, and the opening i+1 (the upper opening in FIG. 3A) travels at the same constant speed, but leads by a certain amount (due to an earlier delivered fluence pattern, for example). The resulting output fluence will have a shape as depicted in FIG. 3B, because the tongue of leaf pair i+1 will be present in the opening of leaf pair i (the leaves are oriented with their tongues toward the lower indices and the grooves toward the higher indices). To minimize the exposure of the tongue of leaf pair i+1, a constant compensating function $C_{i+1}(x) = c$ can be added to the trajectories of leaf pair i+1. This addition effectively delays the leaves in pair i+1, such that the two openings become aligned (FIG. 3C). As seen in FIG. 3D, when the openings are aligned, the tongue and groove effect between the two leaf pairs is eliminated. The following algorithm (I) can be used to minimize the tongue and groove effect:

1. Obtain an MLC sequence from external leaf-sequencing algorithm.
2. Add compensating functions $C_i(x)$ to leaf coordinates $a_i(x)$ and $b_i(x)$, respectively for all leaf pairs i, so that mechanical limitations of the MLC are respected and
    a. the non-weighted $TNG = \Sigma TNG_i$, as given above, is minimized, or
    b. time-dependent weights w(t) are used, and the resulting tongue and groove expression $\int w(t) tng(t) dt$ is minimized.
    c. position-dependent weights $w_y(x)$ and $w_y^c$ are used, and the resulting tongue and groove expression $$\sum_y w_y^c \int w_y(x) tng_y(x) dx$$

is minimized, or
    d. time and position-dependent weights, $w_y(t,x)$ and $w_y^c(t)$ are used, and the resulting tongue and groove expression $$\sum_y w_y^c(t) \int w_y(t, x) tng_y(x) dx$$

is minimized, or
    e. the total treatment time is minimized, or
    f. the changes to the original MLC sequence are minimized, or
    g. the tongue and groove distribution variance in spatial coordinates is minimized, or
    h. the tongue and groove distribution variance in temporal coordinates is minimized, or
    i. any combination of above approaches is used.

Time-dependent weights are useful in cases where the dose rate varies with time, where the target fluence changes with time (i.e. "3D fluence"), or where the target region within the patient moves. If there is significant movement, which causes blurring, the avoidance of striping patterns looses significance and that degree of freedom can be used elsewhere, such as wherever the movement is smaller and striping is more important. Position-dependent weights may be useful in several ways, such as with minimum-leaf-gap-effect optimization, with three-dimensional organ arrangements where the fluence is to be delivered, or with a rotational fluence delivery (although optimal fluence is stationary with respect to the patient, the rotation of the collimator causes the fluence to appear rotational from the perspective of leaf-motion calculation). For example, when there are areas where no fluence should be delivered, but some fluence leaks through due to minimum-leaf-gap effects, minimum-leaf-gap-effect optimization attempts to minimize this leakage effect, usually by forcing a maximum leaf speed. In this example, the tongue-and-groove minimization weight could be set to zero in order to preserve the minimum-leaf-gap-effect optimization.

FIGS. 6A-6F show a simple non-weighted sliding window tongue and groove optimization for a single leaf pair, which is also used in the sample algorithm below. The position x is on the horizontal axis and time (MU) is on the vertical axis. It is assumed that leaves 60 have their tongue direct towards the leaves 62. In other words, the gray area in the figures corresponds to the exposed tongue.

Figure 6A:
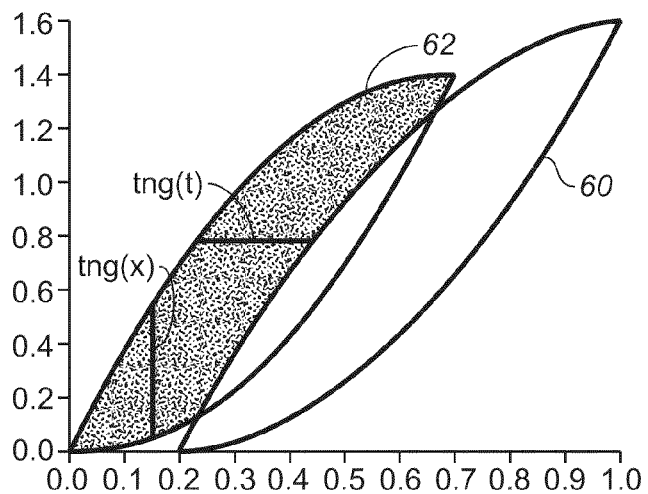
FIGS. 6A-6F show a simple non-weighted sliding window tongue and groove optimization for a single leaf pair.
Figure 6B:
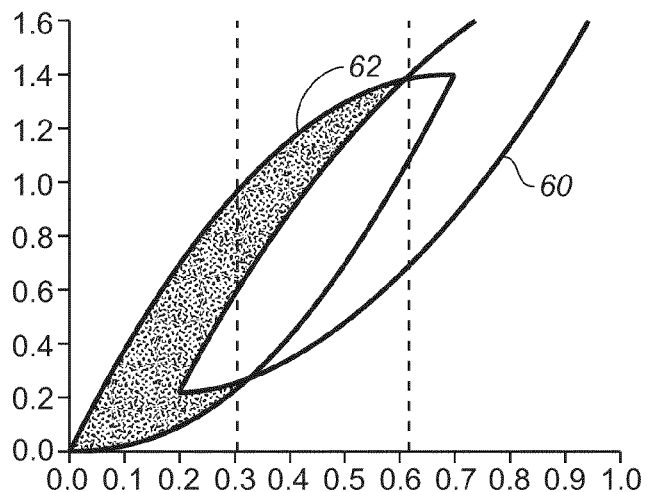
Figure 6C:
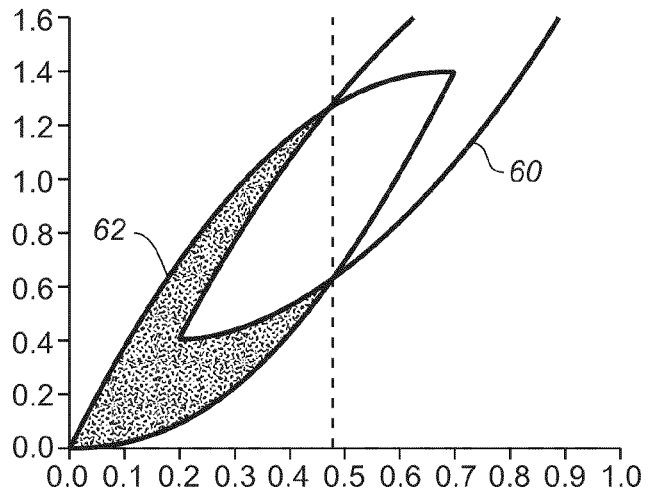

FIGS. 6A-6C relate to a case where a constant delay function is used. FIG. 6A shows the original trajectories of i+1 leaves 60 and i leaves 62, to which the present method is then applied. The vertical bar denotes the amount of total (time-integrated) exposed tongue at location x. The horizontal bar denotes the total width of the tongue exposed at time t. In FIG. 6B, the total amount of tongue and groove effect is reduced by delaying the leaves 60 (i.e. shifting them upwards in the figure) by a constant amount. However, the shift is not optimal for a pure tongue and groove minimization, as can be seen from the intersection points for the leaves that occur at different positions x, indicated by the vertical bars. In contrast in FIG. 6C, where no weighting was used and no other optimization objectives were in place, the optimal solution is a shift that makes the A leaves and the B leaves coincide at the exact same location, denoted by the single vertical bar.

Figure 6D:
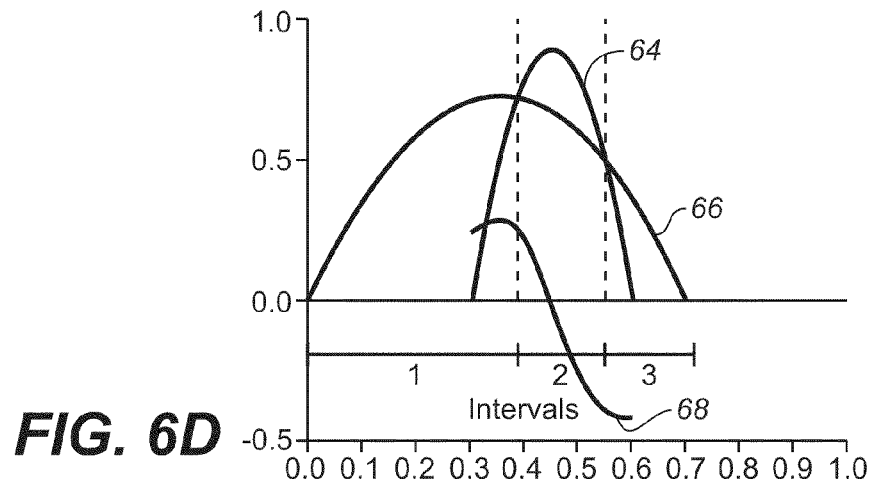
Figure 6E:
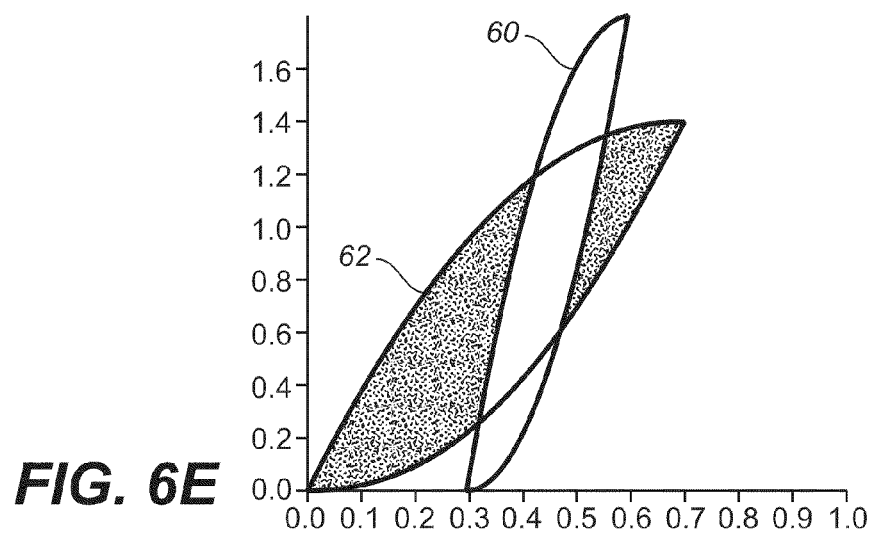
Figure 6F:
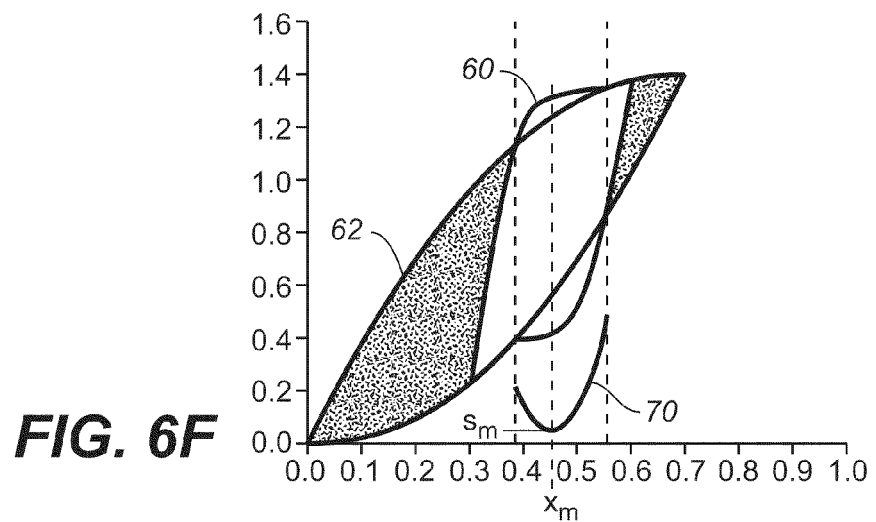

FIGS. 6D-6F relate to a case where a non-constant delay function is needed. Curve 64 and curve 66 in FIG. 6D represent the fluences to be delivered for leaf pairs i+1 and i, respectively. An example delivery of those fluences is shown in FIG. 6E. By adding the non-constant delay function, curve 68 in FIG. 6D, the optimal solution shown in FIG. 6F is found. The optimal delay function is generated by the prototype algorithm described below. In this case there are two positions where the fluences have the same value, resulting in two matching points. The curve 70 in FIG. 6F shows the slack function s(x), further described below.

EXAMPLE

A sliding window tongue and groove optimization is presented as a simple sample of algorithm (I). No weighting is used and the MLC is coplanar, thus the leaf pairs are well defined. It is also assumed that the tongue of leaf pair i+1 is directed towards leaf pair i. The example sliding window moves from left to right.

1. Set i=1.
2. Find fluence crossings between fluences i and i+1. Denote the resulting intervals $I_k$ (FIG. 6D shows intervals 1, 2 and 3), and define the starting and stopping positions: $I_k=[x_0,x_1]$.
   a. if $F_{i+1}(I_k) \leq F_i(I_k)$, as shown in intervals 1 and 3 in FIG. 6D, then, in that interval, set either
      i. $C_{i+1}(x)=a_i(x)-a_{i+1}(x)$, which aligns the A leaves for such an interval, as in interval 1 in FIG. 6D, or,
      ii. $C_{i+1}(x)=b_i(x)-b_{i+1}(x)$, which aligns the B leaves for such an interval, as in interval 3 in FIG. 6D, or,
      iii. $C_{i+1}(x)=[a_i(x)-a_{i+1}(x)]\cdot(1-r)+[b_i(x)-b_{i+1}(x)]\cdot r$, which makes the i+1 leaves travel in between i leaves. The parameter r controls this, and may also be position dependent, r=r(x). In complex cases it may be helpful, but not necessary, to use an r that increases linearly from 0 to 1 during the interval $I_k$. This causes the A leaves to be aligned at $x_0$ and B leaves at $x_1$.

Note that the choice between the conditions i, ii, and iii for $C_{i+1}(x)$ is arbitrary. For example, one can always set $C_{i+1}(x)$ to the same condition.

b. if $F_{i+1}(I_k) > F_i(I_k)$, then
   i. calculate the slack function $s(x)=b_i(x_1)-a_i(x_0)-[b_{i+1}(x)-a_{i+1}(x)]$, and find its minimum value $$s_m = \min_{x \in I_k}(s(x))$$

(see FIG. 6F) and position $x_m$:$s(x_m)=s_m$, then,
in the subinterval $[x_0,s_m]$, set
$C_{i+1}(x)=a_i(x_0)-a_{i+1}(x)+s_m \cdot l_0(x)$, where $l_0(x)$ is a linear function that is zero at $x_0$ and $(s_m-x_0)/(x_1-x_0)$ at $s_m$.
in the other subinterval, $[s_m,x_1]$, set
$C_{i+1}(x)=b_i(x_1)-b_{i+1}(x)+s_m \cdot l_1(x)$, where $l_1(x)$ is a linear function that is $(x_1-s_m)/(x_1-x_0)$ at $s_m$ and zero at $x_1$. This choice of $C_{i+1}(x)$ guarantees maximum leaf speed.

3. If either $C_{i+1}(x)+a_{i+1}(x)=a_{i+1}^{new}(x)$ or $C_{i+1}(x)+b_{i+1}(x)=b_{i+1}^{new}(x)$ (i.e., the new values for coordinate functions), has become decreasing (or too slowly increasing; note the leaf speed limitations) in the interval $I_k$, then define the function $D_{i+1}(x)$ by $\partial_x D_{i+1}(x)=\max\{0, k-\partial_x a_{i+1}^{new}(x), k-\partial_x b_{i+1}^{new}(x)\}$ where $\partial_x$ denotes derivative with respect to x. Using this definition, the functions $a_{i+1}^{new}(x)+D_{i+1}(x)$ and $b_{i+1}^{new}(x)+D_{i+1}(x)$ will always be increasing inside $I_k$, at least with the slope k.

4. Add the function $C_{i+1}(x)$ to coordinates $a_{i+1}(x)$ and $b_{i+1}(x)$.

5. If defined above, add the function $D_{i+1}(x)$ to all $a_j(x)$ and $b_j(x)$ with $j \leq i+1$. Because the same function was added to all leaf pairs that have already been handled, the amount of tongue and groove for those leaf pairs remains optimal, and no re-optimization is needed. Also, because the function $D_{i+1}(x)$ is increasing by definition, it can always be added to any coordinate functions without introducing additional conflicts.

6. If i+1 equals the number of leaves, quit, otherwise set i=i+1 and return to step 2.

This sample algorithm generates an optimal MLC sequence in the sense that the amount of non-weighted tongue and groove defined above is minimized. The sample algorithm is a forward algorithm, meaning that it does not require optimization, and always returns the optimal solution. If there are other objectives, such as those listed in the general algorithm (I), an optimization algorithm is generally required. In addition, in the general method, the reference to the function $C_i(x)$ contains the combined effect of $C_i(x)$ and $D_i(x)$ from all steps in the sample algorithm.

In the traditional sliding window approach, all leaves move in the same direction. However, in general, a leaf sequencing algorithm may produce a movement pattern where the leaves change the direction in which they are moving. For example in the "close-in method," leaves may need to change direction. Thus, in another embodiment of the present invention, algorithm (I) may be modified to include such change-of-direction cases. This modified method uses coordinate functions $a^{-1}(x)$ and $b^{-1}(x)$, which are not well defined in such a case, although the functions a(t) and b(t) are always well-defined.

The following algorithm (II) can be used to minimize the tongue and groove effect in change-of-direction cases:
1. Step 1 remains the same as in algorithm (I).
2. In place of Step 2:
   2.1 Define the sum $S(x_0)$ as follows:
      a. Find solutions of $x_0=a(t)$. Let $X_a^+$ be the set of those solutions for which $a(t)-x_0$ changes sign from negative to positive, and $X_a^-$ the set of those solutions for which a(t) changes sign from positive to negative. Find the corresponding sets $X_b^+$ and $X_b^-$.
      b. Define the sum as $$S(x_0) = \sum_{t_i \in X_b^+} t_i - \sum_{t_i \in X_b^-} t_i - \sum_{t_i \in X_a^+} t_i + \sum_{t_i \in X_a^-} t_i.$$

This sum is the total fluence delivered to position $x_0$, and corresponds to $b^{-1}(x)-a^{-1}(x)$ in the earlier case.
   2.2 Modify functions a(t) and b(t) in such a way, that for each $x_0$ the sum $S(x_0)$ remains constant, so that mechanical limitations of the MLC are respected and apply the list of constraints a through i as in algorithm (I).

It has been suggested that IMRT may also be performed using an MLC having the two opposing leaf banks in different planes. This construction allows many more degrees of freedom than a conventional MLC. For purposes of this description, the non-coplanar MLC has leaves that are aligned to each other, such that the concept of the leaf pair remains well-defined. The optimization of the tongue and groove effect for the more general case of non-aligned leaves, where the leaves still oppose each other, can utilize the same principles, but the notation becomes cumbersome due to the lack of the leaf-pair concept.

In particular, a non-coplanar MLC can have inverted tongues on each bank. In other words, in bank A the tongue of leaf i is directed towards i+1, but in bank B the tongue of i+1 is directed towards i. FIG. 7 illustrates this type of MLC, showing the exposed tongues as dotted lines (e.g., line 72 of bank A and line 74 of bank B). This extra degree of freedom is very useful in tongue and groove optimization.

Returning to FIG. 6C as a starting point, consider how the total amount of the tongue and groove effect can be further minimized in this case. First, the amount of tongue in (x,t) coordinates will be now different (see FIG. 8A), thus the original solution is no longer optimal. It can also be seen that the parking position, i.e., the common position for the closed leaf pair (indicated by the vertical lines in each of FIGS. 8A-8C) is now relevant to the amount of tongue and groove. In this design, the "closed" position need not be common, as was preferred in FIGS. 6A-6C, because the leaves will overlap. For simplicity here, assume that in a "closed" state the irrelevant tongueless leaf will follow the leaf with the tongue. However, in a real implementation, this degree of freedom should be used as well, particularly to provide any additional optimization that is needed.

Figure 8A:
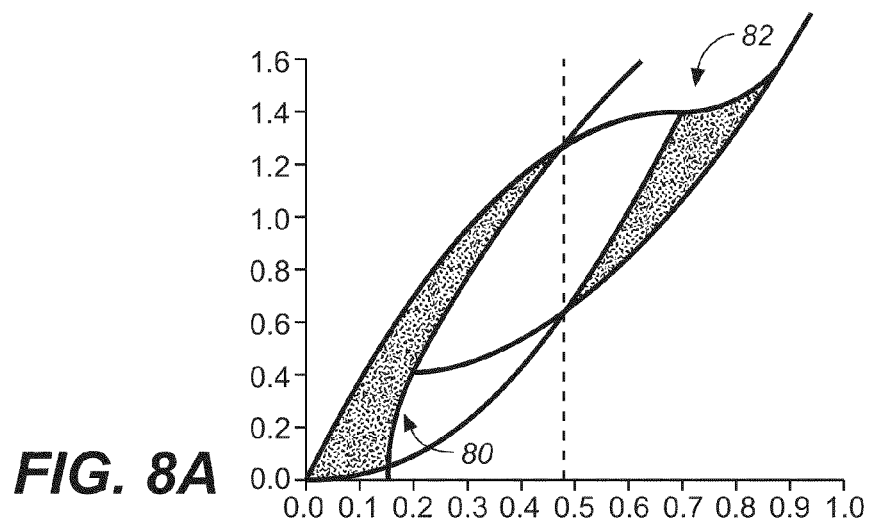
FIGS. 8A-8C show a tongue and groove optimization for a non-coplanar, aligned MLC with inverted tongue and groove design.
Figure 8B:
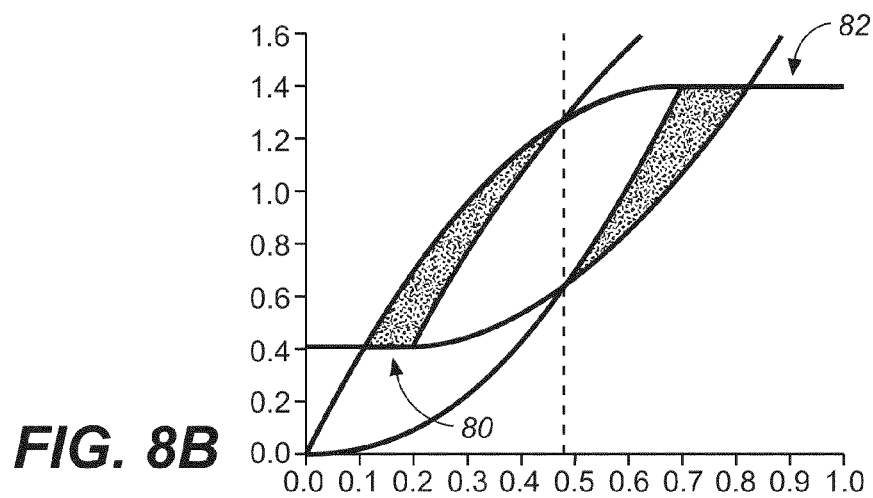
Figure 8C:
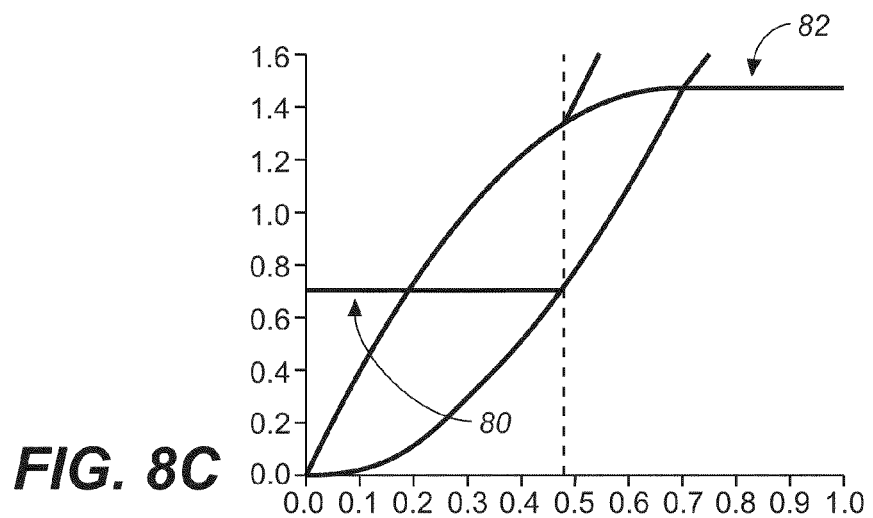

FIGS. 8A-8C further illustrate the case of the non-coplanar, aligned MLC with inverted tongue and groove design, where the entire tongue and groove effect can be avoided. The single lines 80 correspond to the A leaf (i+1), the single lines 82 correspond to the B leaf (i), and, as in FIGS. 6A-6F above, the position x is on the horizontal axis and time (MU) is on the vertical axis. The leaf speed is assumed to be infinite in the figures, but that is not a requirement to completely remove the tongue and groove effect.

Initially, the trajectories of the leaves are as shown in FIG. 8A. The first improvement changes the parking position such that the tongue and groove effect is reduced as in FIG. 8B. The second improvement realigns the B leaves and the A leaves. In this case, aligning the B leaves in the area to the left of the vertical line results in a decreasing a(x). The addition of the function D(x) to all coordinate functions in the area [0.20, 0.48] corrects for the decreasing a(x), as discussed in the prototype algorithm above. These modifications produce the trajectories shown in FIG. 8C, where there is no remaining tongue and groove effect at all. Similarly, for the case presented in FIGS. 6D-6F, the whole tongue and groove effect can be avoided by the application of this method. Accordingly, for a non-coplanar MLC design the tongue and groove effect can be completely avoided for the entire dynamic MLC sequence.

Although most of the techniques presented above apply specifically to dynamic IMRT delivery, some of them are useful in static IMRT pattern calculations as well. For example, a penalty function may be used that favors apertures with a low tongue and groove effect. This approach is particularly useful in MLCs that have an inverted tongue and groove design.

What is claimed is:

1. A method of providing intensity modulated radiation therapy to a target region wherein the tongue and groove effect is minimized, comprising:
   obtaining a multi-leaf collimator (MLC) sequence from an external leaf-sequencing algorithm; and
   modifying the MLC sequence to compensate for the tongue and groove effect, wherein modifications are selected such that mechanical limitations of the MLC are not exceeded and at least one of the following is minimized:
      a non-weighted sum of the tongue and groove effects,
      a weighted sum of the tongue and groove effects using time-dependent weighting,
      a weighted sum of the tongue and groove effects using position-dependent weighting,
      a weighted sum of the tongue and groove effects using time- and position-dependent weighting,
      the tongue and groove effect distribution variance in spatial coordinates, or
      the tongue and groove effect distribution variance in temporal coordinates.

2. The method of claim 1, wherein the step of modifying the MLC sequence includes adding compensating functions $C_i(x)$ to leaf coordinates $a_i(x)$ and $b_i(x)$ for all leaf pairs i.

3. The method of claim 1, wherein the step of modifying the MLC sequence includes minimizing the weighted sum of the tongue and groove effects using time-dependent weighting, further comprising a target fluence that changes with time.

4. The method of claim 1, wherein the step of modifying the MLC sequence includes minimizing the weighted sum of the tongue and groove effects using time-dependent weighting and wherein the target region is in motion.

5. The method of claim 1, wherein the step of modifying the MLC sequence includes minimizing the weighted sum of the tongue and groove effects using position-dependent weighting and wherein the position-dependent weights are generated by minimum-leaf-gap-effect optimization.

6. The method of claim 1, wherein the step of modifying the MLC sequence includes minimizing the weighted sum of the tongue and groove effects using position-dependent weighting and wherein the position-dependent weights are generated by three dimensional organ arrangements in the target region.

7. The method of claim 1, wherein the step of modifying the MLC sequence includes minimizing the weighted sum of the tongue and groove effects using position-dependent weighting and wherein the position-dependent weights are generated by a rotational fluence.

8. The method of claim 1, wherein the step of modifying the MLC sequence further comprises selecting compensating functions such that the total treatment time is minimized.

9. The method of claim 1, wherein the step of modifying the MLC sequence further comprises selecting compensating functions such that changes to the original MLC sequence are minimized.

10. A computer readable medium including a computer program for controlling a multi-leaf collimator (MLC) to provide intensity modulated radiation therapy to a target region wherein the tongue and groove effect is minimized, comprising:

software code executable on a computer to:

obtain a multi-leaf collimator (MLC) sequence from an external leaf-sequencing algorithm; and modify the MLC sequence to compensate for the tongue and groove effect, wherein modifications are selected such that mechanical limitations of the MLC are not exceeded and at least one of the following is minimized:

a non-weighted sum of the tongue and groove effects, a weighted sum of the tongue and groove effects using time-dependent weighting, a weighted sum of the tongue and groove effects using position-dependent weighting, a weighted sum of the tongue and groove effects using time- and position-dependent weighting, the tongue and groove effect distribution variance in spatial coordinates, or the tongue and groove effect distribution variance in temporal coordinates.

11. The computer readable medium of claim 10, wherein the software code executable on a computer to modify the MLC sequence adds compensating functions $C_i(x)$ to leaf coordinates $a_i(x)$ and $b_i(x)$ for all leaf pairs i.

12. The computer readable medium of claim 10, wherein the software code executable on a computer to modify the MLC sequence selects compensating functions to minimize at least one of the total treatment time or changes to the original MLC sequence.

* * * * *